US009003866B2

(12) United States Patent
Tsuzuki et al.

(10) Patent No.: US 9,003,866 B2
(45) Date of Patent: Apr. 14, 2015

(54) GAS SENSOR

(75) Inventors: Masao Tsuzuki, Kakamigahara (JP); Takaya Yoshikawa, Kasugai (JP)

(73) Assignee: NGK Spark Plug Co., Ltd., Aichi (JP)

( * ) Notice: Subject to any disclaimer, the term of this patent is extended or adjusted under 35 U.S.C. 154(b) by 277 days.

(21) Appl. No.: 13/295,291

(22) Filed: Nov. 14, 2011

(65) Prior Publication Data
US 2012/0118039 A1 May 17, 2012

(30) Foreign Application Priority Data

Nov. 12, 2010 (JP) .................................. 2010-253403
Oct. 11, 2011 (JP) .................................. 2011-223562

(51) Int. Cl.
*G01N 7/00* (2006.01)
*G01N 27/407* (2006.01)

(52) U.S. Cl.
CPC .................................. *G01N 27/4077* (2013.01)

(58) Field of Classification Search
USPC ............... 73/23.31, 31.05; 204/424, 426, 428
See application file for complete search history.

(56) References Cited

U.S. PATENT DOCUMENTS

| 4,096,050 | A | * | 6/1978 | Kobayashi et al. | ............ 204/428 |
| 4,199,424 | A |   | 4/1980 | Teitelbaum et al. | |
| 5,711,863 | A | * | 1/1998 | Henkelmann et al. | ........ 204/428 |
| 6,346,179 | B1 | * | 2/2002 | Makino et al. | ................ 204/428 |
| 6,631,632 | B2 |   | 10/2003 | Matsubara et al. | |
| 6,742,379 | B2 |   | 6/2004 | Matsubara et al. | |
| 7,267,117 | B2 |   | 9/2007 | Tonetti et al. | |
| 7,493,796 | B2 | * | 2/2009 | Wilde | .......................... 73/23.31 |
| 7,560,012 | B2 | * | 7/2009 | Shichida et al. | ............. 204/428 |
| 7,708,869 | B2 | * | 5/2010 | Yamada | ........................ 204/428 |
| 7,758,736 | B2 | * | 7/2010 | Okumura et al. | ............. 204/428 |
| 7,793,534 | B2 | * | 9/2010 | Grosse Bley | ................ 73/31.04 |
| 7,901,556 | B2 | * | 3/2011 | Yamada | ........................ 204/428 |
| 8,764,955 | B2 | * | 7/2014 | Yoshikawa et al. | ........... 204/424 |
| 2006/0000258 | A1 | * | 1/2006 | Kim | ............................. 73/23.32 |
| 2008/0016948 | A1 | * | 1/2008 | Yamada | ....................... 73/31.05 |
| 2008/0223110 | A1 | * | 9/2008 | Weyl et al. | ................... 73/31.05 |
| 2009/0101503 | A1 | * | 4/2009 | Kanao | ............................ 204/424 |
| 2009/0188813 | A1 | * | 7/2009 | Kato et al. | ..................... 205/781 |
| 2011/0138881 | A1 | * | 6/2011 | Jones et al. | .................. 73/31.06 |
| 2011/0209523 | A1 | * | 9/2011 | Otsubo et al. | ................ 73/23.31 |
| 2011/0239739 | A1 | * | 10/2011 | Katou et al. | ................. 73/31.05 |
| 2013/0068616 | A1 | * | 3/2013 | Inoue et al. | .................... 204/424 |

FOREIGN PATENT DOCUMENTS

| DE | 102007042975 A1 | 3/2009 |
| EP | 0042436 A1 | 12/1981 |
| EP | 2341334 A1 | 7/2011 |
| GB | 2030304 A | 4/1980 |
| JP | 10-293113 A | 11/1998 |
| JP | 2005-061420 A | 3/2005 |
| JP | 2006-002761 A | 1/2006 |
| WO | WO 2010-050146 A1 | 5/2010 |

\* cited by examiner

*Primary Examiner* — Peter Macchiarolo
*Assistant Examiner* — Mohammed Keramet-Amircola
(74) *Attorney, Agent, or Firm* — Sughrue Mion, PLLC

(57) ABSTRACT

A gas sensor including a detecting element; and a protector having a tube portion surrounding the detecting portion, and a bottom portion the protector having a first opening disposed at the tube portion and a second opening at the bottom portion. The bottom portion includes first and second bottom wall portions, the second bottom wall portion protrudes toward the leading end side, and at least a part of the inner face thereof is located at the leading end side with respect to the outer face of the first bottom wall portion. The second opening is provided on a side opposite the inner space of the tube portion in a communication passage formed by the inner face of the second bottom wall portion, and an opening area of the second opening is larger than an area of the largest imaginary circle that can be placed inside the first opening.

8 Claims, 7 Drawing Sheets

FIG. 11A
| No | L2/L1 | NUMBER OF OK PRODUCTS |
|---|---|---|
| 1 | - | 3 |
| 2 | 0.25 | 3 |
| 3 | 0.5 | 5 |
| 4 | 0.75 | 5 |
| 5 | 1.0 | 5 |
FIG. 11D
| No | L2/L1 | NUMBER OF OK PRODUCTS |
|---|---|---|
| 6 | - | 0 |
| 7 | 0.5 | 0 |
| 8 | 0.75 | 1 |
| 9 | 1.0 | 4 |
| 10 | 1.5 | 5 |
| 11 | 2.0 | 5 |
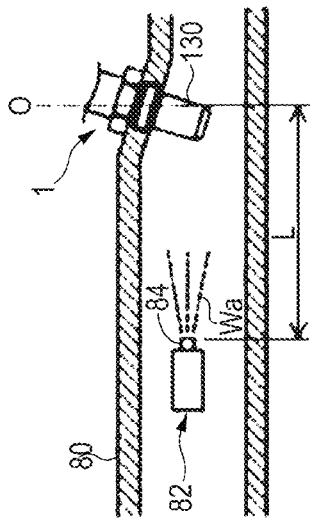
FIG. 11B
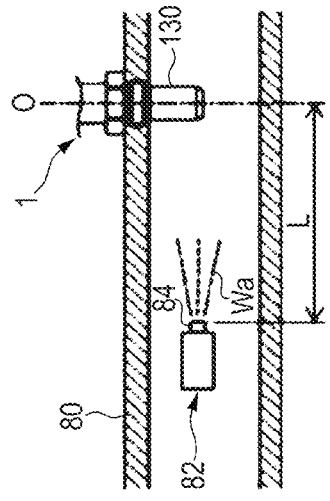
FIG. 11E
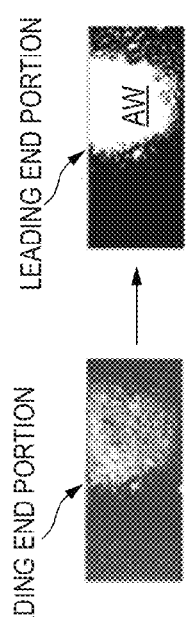
FIG. 11C
(C-1) BEFORE IMAGE TREATMENT → (C-2) AFTER IMAGE TREATMENT

GAS SENSOR

BACKGROUND OF THE INVENTION

1. Field of the Invention

The present invention relates to a gas sensor disposed in an intake passage, such as an intake gas passage through which intake gas drawn into an internal combustion engine from the outside flows, or an intake recirculation gas passage through which intake recirculation gas, which is exhaust gas recirculated to reduce the exhaust of pollutants from an internal combustion engine, flows.

2. Description of the Related Art

A technique is known in which a gas sensor is disposed at an intake gas passage in an internal combustion engine to detect the oxygen concentration of intake gas (atmosphere) drawn into the internal combustion engine from the outside. The detected oxygen concentration is used for the operation control of the internal combustion engine, thereby improving the precision and the like of the air-fuel ratio control of the internal combustion engine (see, for example, Patent Document 1).

In addition, in recent years, a technique in which exhaust gas is reintroduced into an intake system in order to reduce nitrogen oxides (NOx) exhausted from an internal combustion engine (hereinafter referred to as "exhaust gas recirculation" or "EGR system") is known (for example, refer to Patent Document 2). Providing a gas sensor at an intake recirculation gas passage in order to detect the oxygen concentration of intake recirculation gas, which is a mixture of the exhaust gas and intake gas of the EGR system, is also known.

As a gas sensor mounted in an intake passage, such as an intake gas passage or an intake recirculation gas passage, for example, a gas sensor having a detecting element in which the intensity of the electromotive force or the resistance value varies with the concentration of NOx (nitrogen oxides), oxygen, and the like is known (for example, refer to Patent Document 3). Since this gas sensor is exposed to high-temperature gas, such as intake gas or intake recirculation gas, and moisture included in the gas attaches to the gas sensor (the gas sensor is covered with water), there is a concern that the detecting element may be subjected to thermal shock, and cracking or fracturing may occur. Therefore, a protector that covers the detecting element is mounted in the gas sensor so as to protect the detecting element from being covered with water. Furthermore, while gas flowing toward the intake passage side includes more soot (carbon) than gas flowing toward the exhaust passage, the protector can also prevent the soot from attaching to the detecting element, and can prevent the detecting precision of the detecting element from being degraded.

In addition, under the assumption that the protector has a dual structure of an inside protector and an outside protector, a gas sensor having an external gas introducing portion for introducing intake gas to the inside of the protector provided on the side face of the tube-shaped portion of the outside protector and an external gas releasing portion for releasing the intake gas from the inside of the protector disposed at the bottom portion (leading end face) of the outside protector is known (see, for example, Patent Document 4). Thereby, even when the external gas introducing portion is made relatively large in consideration of clogging in the external gas introducing portion, soot attaches to the inner wall portion of the inside protector, and attachment of soot to the detecting element can be suppressed. As a result, clogging of the external gas introducing portion can be suppressed (degradation of the detecting precision of the detecting element is suppressed), and the occurrence of fracturing or cracking in the detecting element can also be suppressed.

RELATED ART DOCUMENT

[Patent Document 1] JP-A-2005-61420
[Patent Document 2] JP-A-2006-2761
[Patent Document 3] JP-A-H10-293113
[Patent Document 4] International Publication No. 2010/050146

Problems Solved by the Invention

Meanwhile, in the gas sensor disposed at an intake passage in an internal combustion engine, when the gas releasing portion (opening) is relatively small, soot blocks the gas releasing portion of the protector so as to cause clogging, and the detecting precision of the detecting element is degraded. However, since the gas releasing portion is necessarily provided at the leading end (bottom portion) of the protector in order to rapidly exchange gases to be measured, when the gas releasing portion is relatively large, there is a concern that water may intrude into the inside of the protector from a gas releasing hole such that the detecting element may be covered with water, and cracking or fracturing may occur in the detecting element.

SUMMARY OF THE INVENTION

The invention has been made to address the above problems of the prior art, and an object of the invention is to suppress the detecting element from being covered with water and to suppress clogging the opening provided at the bottom portion of the protector.

The above object of the invention has been achieved by providing a gas sensor adapted for disposing in the intake passage of an internal combustion engine, which comprises a detecting element extending in an axial direction and comprising a detecting portion for detecting a specific gas component in a gas to be measured on a leading end side of the gas sensor; and a protector having a tube portion surrounding the detecting portion from outside in a radial direction and a bottom portion coupled with a leading end side of the tube portion, the protector having a first opening which is disposed at the tube portion so as to face the downstream side of an intake passage in the internal combustion engine, and which allows the gas to be measured to flow into the tube portion, and a second opening at the bottom portion through which the gas to be measured flows, and wherein the bottom portion includes a first bottom wall portion and a second bottom wall portion, the second bottom wall portion protrudes toward the leading end side in the axial direction, and at least a part of an inner face of the second bottom wall is located at the leading end side in the axial direction with respect to an outer face of the first bottom wall portion, the second opening facing the downstream side of the intake passage is provided on a side opposite the inner space of the tube portion in a communication passage formed by the inner face of the second bottom wall portion, and the communication passage is formed so that an opening area of the second opening is larger than an area of a largest imaginary circle that can be placed inside the first opening when the first opening is viewed planarly in a direction perpendicular to the central axis of the tube portion.

According to the above gas sensor, since the second opening is formed at the bottom portion located on the leading end side of the protector, the gas to be measured is rapidly released from inside to the outside of the protector through the second opening, and degradation in responsiveness can be suppressed.

In addition, the second bottom wall portion, which is a part of the bottom portion, protrudes toward the leading end side, and the communication passage connecting the inner space of the tube portion and the outside of the protector is formed by the inner face of the second bottom wall portion. In addition, the second opening, which is an opening formed by portions of the end circumferences of the first bottom wall portion and the second bottom wall portion, is formed on the side opposite the inner space of the tube portion in the communication passage, and the second opening faces the downstream side of the intake passage. This configuration can suppress intrusion of moisture, oil or the like into the inner space of the protector which flows from the upstream side of the intake passage or the side face direction of the protector.

Therefore, since intrusion of moisture and the like from the second opening can be suppressed even when the second opening is relatively large, it is possible to make the second opening large enough to suppress clogging due to soot. Therefore, it is possible to prevent the second opening from becoming clogged due to soot by making the opening area of the second opening larger than the area of the largest imaginary circle that can be placed inside the first opening when the first opening is viewed planarly in a direction perpendicular to the central axis of the tube portion.

Meanwhile, in the protector of the invention having the first opening facing the downstream side of the intake passage and the second opening provided at the tube portion and the bottom portion respectively, the majority of the gas to be measured flowing through the inside of the protector is introduced to the inside of the protector through the first opening, and released to the outside of the protector through the communication passage and the second opening. Therefore, the amount of soot intruding into the inside of the protector is proportionate to the size of the first opening. Therefore, it is possible to suppress clogging due to soot by setting the opening area of the second opening (gas releasing portion) in accordance with the size of the first opening (gas introducing portion).

In summary, the invention can suppress cracking or fracturing in the detecting element, which is caused by water covering the detecting element and the like, rapidly exchange gases to be measured, and can suppress the second opening from being clogged due to soot, whereby it is possible to suppress degradation of the detecting precision of the detecting element.

Meanwhile, in the invention, when "the largest imaginary circle that can be placed inside the first opening" is taken into account, specifically, the imaginary circle may be seen from "the direction in which the opening area appears to be largest when the first opening is viewed planarly from the outside of the protector." Similarly, even when the opening area and shape of the second opening are taken into account, the opening area and shape of the second opening may be seen from "the direction in which the opening area appears to be largest when the second opening is viewed planarly from the outside of the protector."

In addition, the fact that the first opening and the second opening "face the downstream side of the intake passage" refers to the fact that the respective openings are visible when the gas sensor is disposed in the intake passage, and the gas sensor is viewed from the downstream side of the intake passage.

In addition, when the gas sensor is viewed from the upstream side of the intake passage, the second opening is blocked by the outer face of the second bottom wall portion (and in turn has a configuration that is not visible).

Furthermore, the minimum value L1 of the distance between a first end portion farthest separated from the end edge of the second opening in the second bottom wall portion and the first bottom wall portion in the diameter direction of the protector and the minimum value L2 of the distance between the first end portion and the end edge of the second opening in the second bottom wall portion in the diameter direction of the protector preferably satisfy a relationship of L2/L1≥0.5.

Forming the second opening in the above manner makes the distance of the inner space of the protector, which is visible when the gas sensor is seen from the bottom portion side along the central axis of the protector in the radial direction of the protector, half or less the distance when the second opening is formed along the central axis of the protector as in the related art. Therefore, it is possible to more effectively suppress intrusion of moisture and the like into the inside of the gas sensor, and to further effectively suppress cracking or fracturing in the detecting element.

More preferably, the relationship L2/L1≥1.0 is satisfied.

Forming the second opening in the above manner makes the second opening and the inner space of the protector invisible when the gas sensor is seen from the leading end side along the central axis of the protector. Therefore, there is little concern that moisture may intrude into the inside of the protector even when water is applied to the protector along the central axis of the protector from the leading end side. Therefore, it is possible to more effectively suppress intrusion of moisture and the like into the inside of the gas sensor, and to further effectively suppress cracking or fracturing in the detecting element.

In addition, the second opening preferably has a size large enough to include the entire imaginary circle. In addition, desirably, the aspect ratio of the second opening is 5 or less, or the bottom of the protector has a single (one and only one) second opening.

This is because clogging in the second opening due to soot is related not only to the area of the opening, but also to the shape of the opening as soot accumulates from the circumferential edge portion of the opening so as to block the opening. For example, clogging due to soot is less likely to occur in a small number of relatively large openings than in a large number of relatively small openings, even when the total opening areas are the same. Similarly, clogging due to soot is less likely to occur in substantially circular or square openings than in slit-like openings, even when the opening areas are the same. Therefore, forming the second openings in the above manner can more effectively suppress clogging due to soot.

Meanwhile, the "aspect ratio" of the second opening refers to a ratio of the dimension of the longest opening to the dimension of the longest opening in a direction perpendicular to the longest opening in the projection view of the second opening.

In addition, the invention becomes more effective when the temperature in at least a portion of the protector is 280° C. to 600° C.

Soot, moisture, oil, and the like intrude into the inside of the protector from the first opening, and attach to the inside of the protector. At this time, when the protector temperature is 600° C. or less, the attached soot is not easily combusted (burned off); however, when the protector temperature is 280° C. or more, the attached moisture, oil, and the like are easily evaporated, and the soot attached to the inside of the protector is also dried. As a result, the soot becomes easily separable from the inside of the protector, and the separated soot is exhausted to the outside of the protector mainly from the second opening.

At this time, it is possible to prevent the moisture or soot once attached to the inside of the protector from being included again in gas introduced to the detecting element so as to suppress attachment of the moisture or soot to the detecting element. However, the frequency of clogging in the second opening is slightly increased. According to the configuration of the invention even in the above gas sensor, clogging in the second opening can be suppressed. Meanwhile, the combustion temperature of soot depends on the oxygen concentration, the amount of moisture and soot, and the like in the gas to be measured; however, in general, soot is easily combusted at 600° C. or more.

Meanwhile, the expression "the temperature in at least a portion of the protector is 280° C. to 600° C." means that the temperature is 280° C. to 600° C. at an arbitrary location in the protector when the gas sensor is mounted in the intake passage, and the gas sensor detects a specific gas component in the gas to be measured. It is not necessary for the entire protector to be at a temperature of 280° C. to 600° C. In addition, the protector may be at a temperature of 280° C. to 600° C. by exposure to the gas to be measured, or may be heated to 280° C. to 600° C. using a heater if the gas sensor has a heater that heats the detecting portion. In addition, the temperature of the protector can be measured using a thermocouple or a radiation thermometer.

The invention provides a gas sensor that can suppress clogging due to soot in the second opening provided at the bottom portion of the protector and that can suppress fracturing or cracking due to the detecting element being covered with water.

BRIEF DESCRIPTION OF THE DRAWINGS

Illustrative aspects of the invention will be described in detail with reference to the drawings wherein:

FIGS. 11A to 11E explain experiments which investigate and evaluate the influence of the amount of water covering the leading end portion of the protector and results thereof.

DETAILED DESCRIPTION OF THE PREFERRED EMBODIMENTS

Hereinafter, an embodiment of a gas sensor of the invention is described with reference to the accompanying drawings. However, the present invention should not be construed as being limited thereto.

Figure 1:
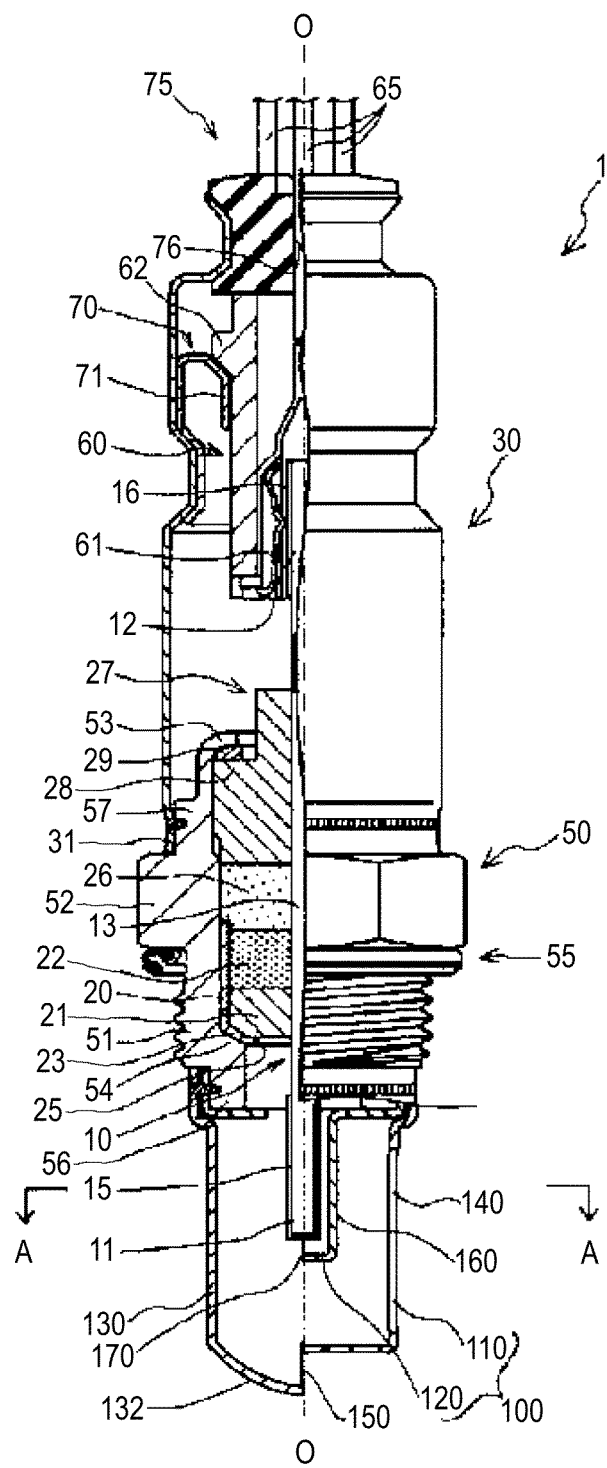
FIG. 1 shows a partial cross-sectional view of the gas sensor 1 of an embodiment of the invention.

Firstly, the structure of the gas sensor 1 as an example will be described with reference to FIG. 1. FIG. 1 is a partial cross-sectional view of the gas sensor 1, in which the axis O direction (shown by a chain line) of the gas sensor 1 indicates the top and bottom direction, and the detecting portion 11 side and the rear end portion 12 side of a detecting element 10 held in the gas sensor indicate a leading end side and rear end side of the gas sensor 1 respectively. Meanwhile, in the embodiment, the detecting element 10 extends in the axial direction along the central axis of a protector 100.

Figure 2:
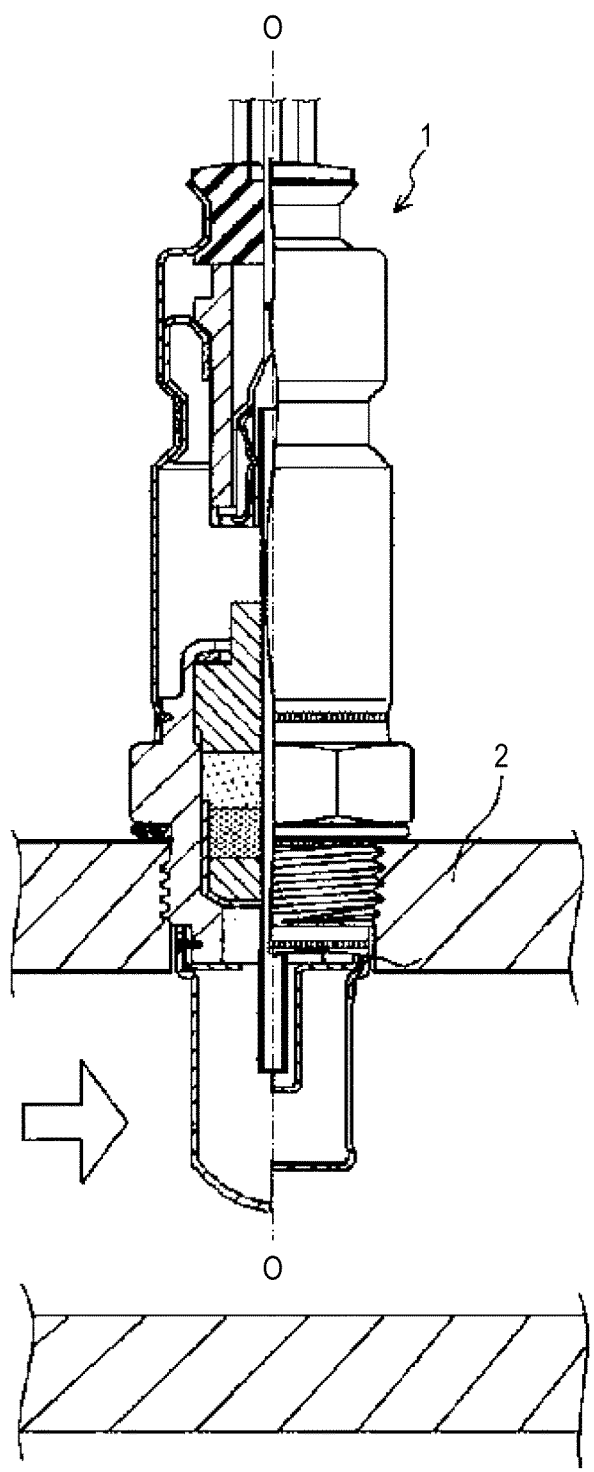
FIG. 2 shows a view of the gas sensor 1 of the embodiment mounted in the intake passage 2.

Meanwhile, the gas sensor 1 is a so-called universal exhaust gas oxygen sensor that is mounted in an intake passage 2 of an internal combustion engine as shown in FIG. 2, in which the detecting portion 11 of the detecting element 10 held inside is exposed to the gas to be measured, such as intake gas, intake recirculation gas, and the like flowing through the intake passage 2, and an air-fuel ratio is detected from the oxygen concentration of the gas to be measured. Meanwhile, the arrow in FIG. 2 shows the flow of the gas to be measured in the intake passage 2, and the "downstream side of the intake passage" as described below indicates the right side in FIG. 2.

The detecting element 10 forms a strip shape extending in the axis O direction as is well known, and is an integrated laminated body in which a gas detecting body that detects oxygen concentration and a heating body that heats and activates the gas detecting body at an early stage are integrated into a substantially rectangular column shape. The gas detecting body is composed of a solid electrolyte body made mainly of zirconia and a detecting electrode made mainly of platinum (both not shown), and the detecting electrode is disposed in the detecting portion 11 formed on the leading end side of the detecting element 10. In addition, a protective layer 15 is formed at the detecting portion 11 of the detecting element 10 so as to cover the outer circumferential face of the detecting electrode in order to protect the detecting element from poisonous substances included in the gas to be measured. Meanwhile, five electrode pads 16 (FIG. 1 shows one of them) are formed at a rear end portion 12 on the rear end side of the detecting element 10 in order to extract the electrode signal from the gas detecting body or the heating body. Meanwhile, while the detecting element 10 is described as the "detecting element" of the invention in the embodiment, strictly, the configuration of the detecting element does not necessarily need to include the heating body, and the gas detecting body corresponds to the "detecting element" of the invention. In addition, the detecting element 10 may assume the shape of a bottomed tube instead of a substantially rectangular column shape as shown in FIG. 1.

A bottomed tube-shaped metal cup 20 made of a metal is disposed slightly on the leading end side of the center of the trunk portion 13 of the detecting element 10 in a state of having the detecting element 10 inserted therethrough so that the detecting portion 11 protrudes from an opening 25 at the tube bottom. The metal cup 20 is a member for holding the detecting element 10 in a metal shell 50, and a leading end circumferential edge portion 23 in the edge portion of the tube bottom is formed in a tapered shape throughout the outer circumferential face. An aluminum ceramic ring 21 and a talc ring 22, which is a compressed and hardened talc powder, are accommodated in the metal cup 20 in a state in which the aluminum ceramic ring and the talc ring are inserted through the detecting element 10. The talc ring 22 is crushed in the metal cup 20 and filled into fine portions, whereby the detecting element 10 is held at a fixed location in the metal cup 20.

The detecting element 10 integrated with the metal cup 20 is held and surrounded by the tube-shaped metal shell 50. The metal shell 50 is for mounting and fixing the gas sensor 1 to the intake passage 2 of a vehicle, made of low-carbon steel, such as SUS 430, and has a male screw portion 51 for mounting the gas sensor in an exhaust pipe or vent pipe formed on the outer circumferential leading end side. A leading end engaging portion 56 with which a protector 100 described below is engaged is formed on the leading end side of the male screw portion 51. In addition, a tool engaging portion 52 with which a mounting tool is engaged is formed at the outer circumferential center of the metal shell 50, and a gasket 55 for preventing gas leakage when the gas sensor is mounted in the intake passage 2 is fittably inserted between the leading end face of the tool engaging portion 52 and the rear end of the male screw portion 51. Furthermore, a rear end engaging portion 57 with which an outer tube 30 is engaged is formed on the rear end side of the tool engaging portion 52, and a swaging portion 53 for swaging and holding the detecting element 10 in the metal shell 50 is formed on the rear end side of the rear end engaging portion.

In addition, a step portion 54 is formed in the vicinity of the male screw portion 51 at the inner circumference of the metal shell 50. The leading end circumferential edge portion 23 of the metal cup 20 which holds the detecting element 10 is locked at the step portion 54. Furthermore, the talc ring 26 is filled into the inner circumference of the metal shell 50 from the rear end side of the metal cup 20 in a state in which the talc ring is inserted through the detecting element 10. In addition, a tube-shaped sleeve 27 is fitted into the metal shell 50 so as to press the talc ring 26 from the rear end side. A step-shaped shoulder portion 28 is formed at the outer circumference of the sleeve 27 on the rear end side, and a toric swaging packing 29 is disposed at the shoulder portion 28. In the above state, the swaging portion 53 of the metal shell 50 is swaged through the swaging packing 29 so that the shoulder portion 28 of the sleeve 27 is pressed toward the leading end side. The talc ring 26 pressed to the sleeve 27 is crushed in the metal shell 50 and filled across the fine portions. Further, the metal cup 20 and the detecting element 10 are held at fixed locations in the metal shell 50 by the talc ring 26, and the talc ring 22 filled in the metal cup 20 in advance. The air tightness in the metal shell 50 is maintained by the swaging packing 29 interposed between the swaging portion 53 and the shoulder portion 28 of the sleeve 27, thereby preventing combustion gas from flowing out.

The rear end portion 12 of the detecting element 10 protrudes backward more than the rear end (swaging portion 53) of the metal shell 50, and the rear end portion 12 is covered with a tube-shaped separator 60 composed of an insulating ceramic. The separator 60 holds five electrode pads 61 formed at the rear end portion 12 of the detecting element 10 and five connection terminals 61 (FIG. 1 shows one of them) that are electrically connected to the electrode pads respectively. Further, the separator 60 accommodates and protects the connection portions of the respective connection terminals 61, and five lead wires 65 (FIG. 1 shows three of them) are pulled to the outside of the gas sensor 1.

In addition, the tube-shaped outer tube 30 is disposed so as to cover and surround the rear end portion 12 of the detecting element 10, in which the separator 60 is fit. The outer tube 30 is made of stainless steel (for example, SUS304), and an opening end 31 on the leading end side of the outer tube is engaged with the outer circumference of the rear end engaging portion 57 of the metal shell 50. The opening end 31 is swaged from the outer circumference side and, furthermore, laser-welded throughout the outer circumference so as to be joined to the rear end engaging portion 57, whereby the outer tube 30 and the metal shell 50 are integrally fixed.

In addition, a tube-shaped metal holding clasp 70 is disposed in a gap between the outer tube 30 and the separator 60. The holding clasp 70 has a supporting portion 71 configured by folding the rear end of the holding clasp 70 inward, and supports the separator 60 by engaging a flange portion 62 with the supporting portion 71. The flange portion 62 is provided in a flange shape at the outer circumference of the separator 60 on the rear end side which is inserted through the inside of the holding clasp 70. In this state, the outer circumferential face of the outer tube 30 where the holding clasp 70 is disposed is swaged, and the holding clasp 70 supporting the separator 60 is fixed to the outer tube 30.

A grommet 75 made of a fluorine-based rubber is fitted in the opening of the outer tube 30 on the rear end side. The grommet 75 has five inserting holes 76 (FIG. 1 shows one of them), and the five lead wires 65 pulled out from the separator 60 are air-tightly inserted through the respective inserting holes 76. In this state, the grommet 75 presses the separator 60 toward the leading end side, and is swaged from the outer circumference of the outer tube 30, thereby being fixed to the rear end of the outer tube 30.

Next, the protector 100, which is an important feature of the invention, will be described.

The protector 100 is fixed to the leading end engaging portion 56 of the metal shell 50 so as to surround the detecting portion 11 of the detecting element 10. The protector 100 prevents soot, moisture, oil, and the like in the gas to be measured from attaching to the detecting element 10. The structure of the protector 100 shown in FIG. 1 will be described in detail with reference to FIGS. 3 to 7.

Figure 3:
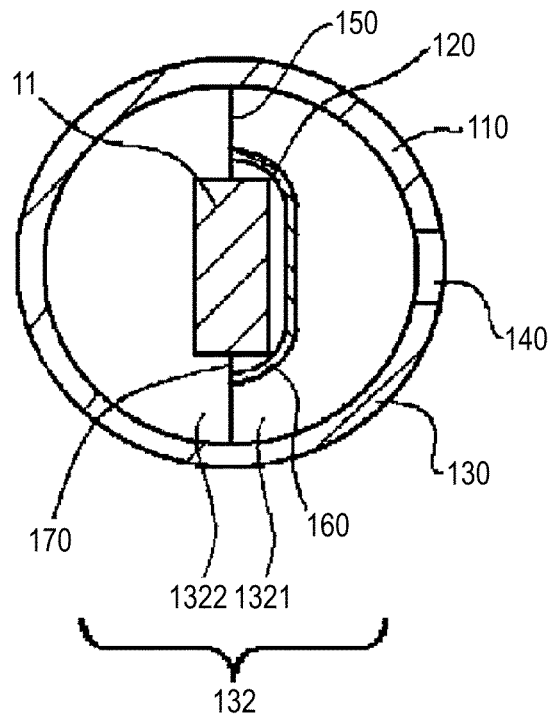
FIG. 3 shows a cross-sectional view of the gas sensor 1 taken along A-A in FIG. 1.

As shown in FIGS. 1 and 3, the protector 100 has a dual structure composed of an inside protector 120 forming a gap (clearance) with the detecting portion 11 of the detecting element 10, and an outside protector 110 forming a gap with the inside protector 120.

Figure 4:
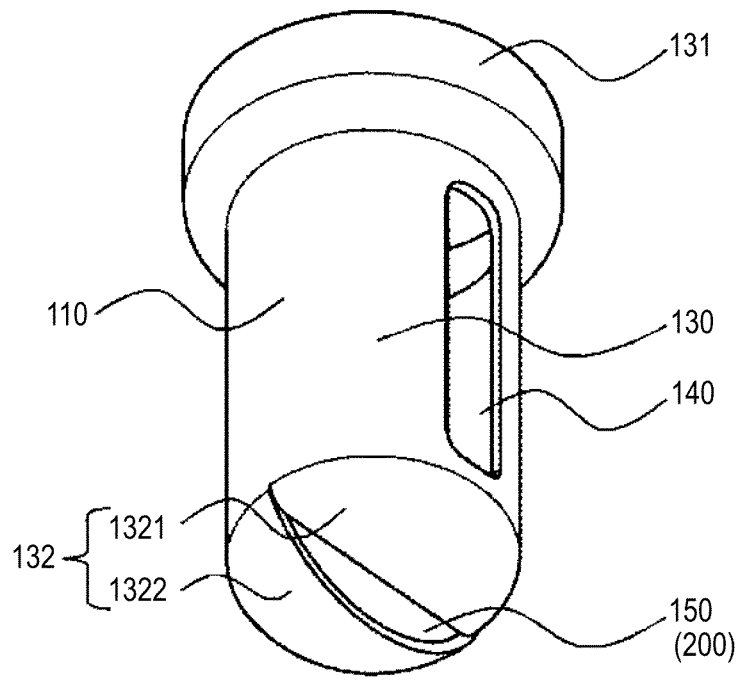
FIG. 4 shows a perspective view of the outside protector 110 of the embodiment.

The outside protector 110 is formed of stainless steel, such as SUS304, and has a substantially tube-shaped outside tube portion 130 that extends in the axial direction and surrounds the detecting element 10 from outside in the radial direction, an outside base end portion 131 that is disposed on the rear end side of the outside tube portion 130 in the axial direction and has a larger outer diameter than the outside tube portion 130, and an outside bottom portion 132 that is connected to the leading end of the outside tube portion 130 in the axial direction and is disposed at a location where the detecting element 10 is surrounded (covered) from the leading end side in the axis direction as shown in FIGS. 1 and 4.

Meanwhile, the outside tube portion 130 and the outside bottom portion 132 in the embodiment correspond to the "tube portion" and the "bottom portion" of the invention, respectively.

The outside base end portion 131 is engaged with the leading end engaging portion 56 of the metal shell 50, and the entire circumference is welded to the metal shell 50 and the inside protector 120 by laser welding. In addition, the outside tube portion 130 assumes a cylinder shape on the leading end side of the outside base end portion 131, and a single first opening 140, which is a slit-shaped opening extending in the axial direction, is provided on the outer circumferential face. In addition, a second opening 150 is provided at the outside bottom portion 132.

As shown in FIG. 4, the second opening 150 is formed as a protruding part of the outside bottom portion 132, protruding toward the leading end side in the axial direction in a dome shape so as to provide an opening. In the embodiment, among the outside bottom portions 132, a portion present at the same location as the leading end of the outside tube portion 130 is a first bottom wall portion 1321, and a portion which protrudes in a dome shape toward the leading end side in the axial direction to a greater extent than the first bottom wall portion 1321 and has at least a part of an inner face located on the leading end side of the outer face of the first bottom wall portion 1321 in the axial direction is a second bottom wall portion 1322. Meanwhile, the second opening 150 is composed of the first bottom wall portion 1321 and the end edge of the second bottom wall portion 1322.

In addition, the inner face of the second bottom wall portion forms a communication passage 200 such that the inner space of the outside tube portion 130 is in communication with the second opening 150 (and the outside of the protector 100). Meanwhile, specifically, an area formed by the inner face of the second bottom wall portion 1322, the second opening 150, and the plane intersecting the central axis of the protector passing the end edge that forms the second opening 150 of the first bottom wall portion 1321 defines the communication passage 200.

Figure 5:
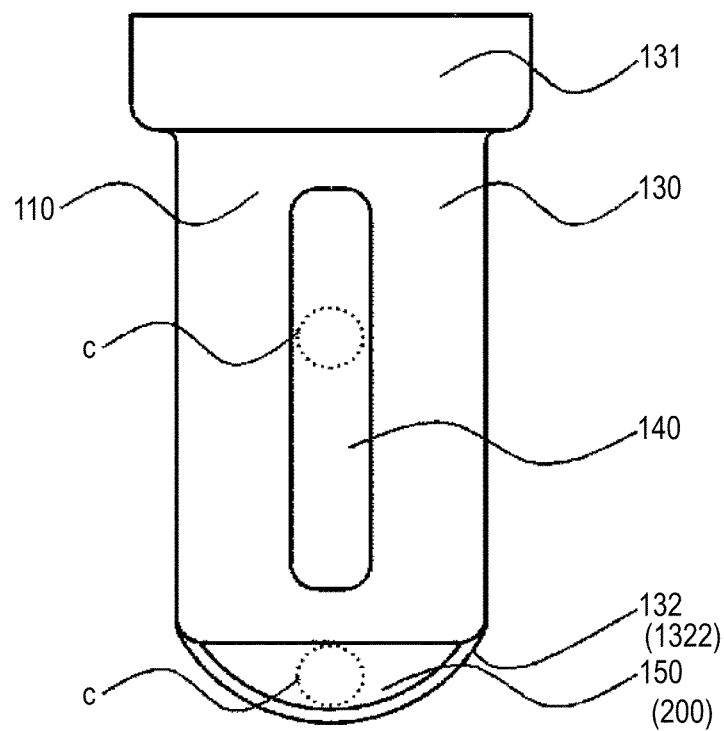
FIG. 5 shows a front view of the outside protector 110 of the embodiment seen from the downstream side of the intake passage 2.

As shown in FIG. 5, the first opening 140 and the second opening 150 are formed so that an imaginary circle C (diameter R), which is the largest circle that can come into contact with the inside of the first opening 140, can also come into contact with the inside of the second opening 150. Therefore, since the second opening 150 forms an opening large enough to exhaust soot that has intruded into the inside of the protector 100 through the first opening 140 to the outside of the protector 100, it is possible to suppress clogging from occurring in the second opening 150.

Meanwhile, here, the fact that the imaginary circle C can come into contact with the inside of each of the openings means that the imaginary circle C can be drawn in the area of each of the openings when the imaginary circle is viewed planarly in the direction in which the opening area of each of the openings appears to be largest.

Figure 6:
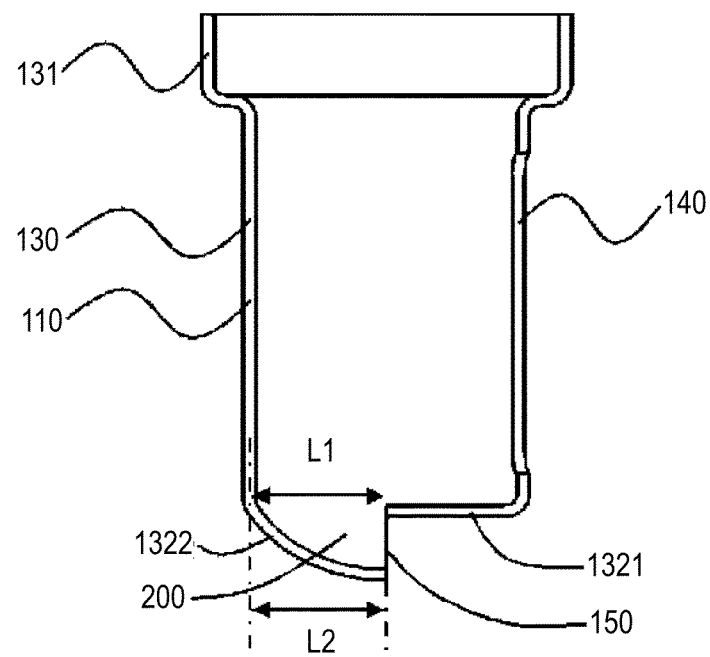
FIG. 6 shows a cross-sectional view of the outside protector 110 of the embodiment.

FIG. 6 shows the enlarged cross-sectional view of the outside protector 110 shown in FIG. 1. The minimum value of the distance between the first end portion farthest separated from the end edge of the second opening among the second bottom wall portions and the first bottom wall portion in the diameter direction of the protector is set to L1. In addition, the minimum value of the distance between the first end portion and the end edge of the second opening among the second bottom wall portions in the diameter direction of the protector is set to L2, and L0=L2/L1.

At this time, in the embodiment, L0=1. Therefore, the second opening 150 and the inner space of the protector 100 have an invisible configuration when the gas sensor 1 is seen from the leading end side along the central axis of the protector. Therefore, it is possible to effectively suppress moisture and the like from intruding into the inside of the protector 100.

In addition, the gas sensor 1 is disposed in the intake passage 2 so that the outside bottom portion 132 faces the leading end side in the vertical direction. In addition, the gas to be measured flows in the intake passage 2 from upstream to downstream (the arrow direction in FIG. 2), and the gas sensor 1 is mounted so that the first opening 140 and the second opening 150 of the outside protector 110 face the downstream side of the intake passage 2. In addition, the second opening 150 faces the downstream side, and is blocked by the outer face of the second bottom wall portion when seen from the upstream side of the intake passage 2.

The gas to be measured flowing through the inside of the protector is drawn in mainly from the downstream side of the intake passage 2, introduced to the inside of the outside protector 110 from the first opening 140, and released from the second opening 150 to the outside of the outside protector 110 through the communication passage 200. In contrast to the above, because soot, moisture and oil flows from upstream to downstream along with the gas to be measured in the intake passage 2, it becomes difficult for soot, moisture, oil, and the like to flow from downstream to upstream in the intake passage 2 so as to be introduced to the outside protector 110. Particularly, the outer face of the second bottom wall portion suppresses moisture and the like flying from the upstream side of the intake passage 2 and the side face side of the protector 100 to intrude into the inside of the protector.

Therefore, it is possible to reduce soot, moisture, oil, and the like introduced to the protector 100 from the outside.

Figure 7:
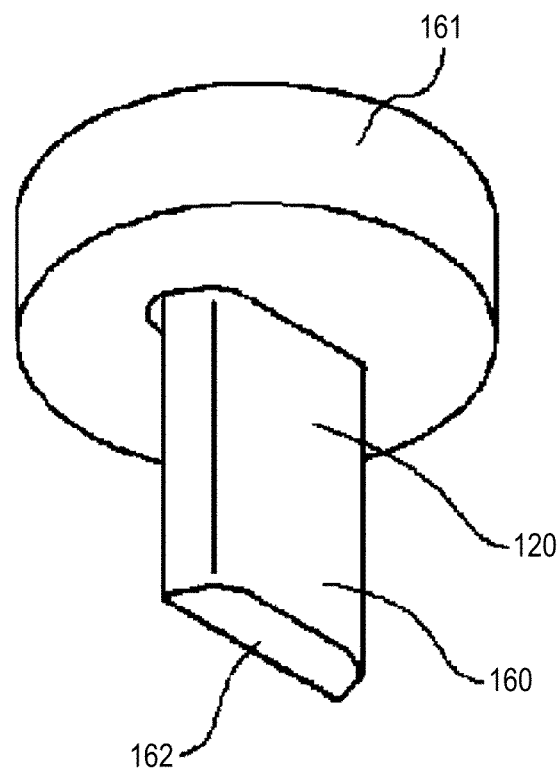
FIG. 7 is a perspective view of the inside protector 120 of the embodiment.

In addition, the inside protector 120 is formed of stainless steel, such as SUS304, and has an inside tube-shaped portion 160 and an inside base end portion 161 with an outer diameter larger than the inside tube-shaped portion 160 as shown in FIGS. 1, 3 and 7. As described above, the inside base end portion 161 is engaged with the leading end engaging portion 56 of the metal shell 50, and welded to the outside base end portion 131 and the metal shell 50 throughout their circumferences by laser welding. Meanwhile, the inside tube-shaped portion 160 is provided in a semicircular arc shape on the leading end side of the inside base end portion 161, and covers the heater side of the detecting portion 11 of the detecting element 10. An inside gas introducing portion 170 is provided at the end portion of the inside tube-shaped portion 160 in the radial direction. In the embodiment, the detecting portion 11 protrudes in the radial direction with respect to the inside gas introducing portion 170, and exposes to the inner space of the outside protector 110. Furthermore, an inside bottom portion 162 is provided on the leading end side of the inside tube-shaped portion 160, so as to cover the leading end of the detecting portion 11 of the detecting element 10. Meanwhile, the inside gas introducing portion 170 of the inside protector 110 is disposed on the upstream side of the intake passage 2 when the gas sensor 1 is disposed in the intake passage 2. However, in the invention, the inside protector 120 is not an essential component.

As such, the second opening 150 is disposed at the leading end of the protector 100 (outside bottom portion 132) so as to face the downstream side of the intake passage 2. Particularly, the second opening 150 is disposed so that the inside of the protector 100 is invisible even when the second opening 150 is viewed along the central axis from the leading end side of the protector 100. It is therefore possible to suppress water from covering the detecting element 10 (or oil from attaching thereto), and thus it becomes possible to open a relatively large the second opening 150. Specifically, by forming the second opening 150 so that the imaginary circle C inside of the second opening 150 has a diameter R drawn when the imaginary circle is viewed planarly in the direction in which the opening area of the second opening 150 appears to be largest, soot that has intruded into the inside of the protector 100 through the first opening 140 can be exhausted without the second opening 150 becoming clogged. Meanwhile, the aspect ratio of the second opening 150 is about 4.2 in the embodiment.

As a result, since occurrence of cracking or fracturing of the detecting element 10 due to water covering the detecting element and the like can be suppressed, the gas to be measured can be rapidly exchanged, clogging of the gas releasing hole 150 due to soot can be suppressed, and degradation of the detecting precision of the detecting element 10 can be suppressed.

In addition, the protector 100 in the embodiment carries out heating in conjunction with the heating body that composes the detecting element 10 when the gas sensor 1 is detecting specific gas components in intake gas (during actual use of the gas sensor 1). Consequently, the temperature of the inside protector 120 becomes higher than the temperature of the outside protector 110. Specifically, the temperature of the inside protector 120 becomes 350° C., and the temperature of the outside protector 110 becomes 120° C. Thereby, it is possible to evaporate moisture, oil, and the like attached to the inside tube-shaped portion 160 or to remove soot from the inside tube-shaped portion 160. Soot separated from the inside protector is exhausted to the outside of the protector through the second opening 150 disposed on the leading end side of the outside protector 110 (outside bottom portion 132). As a result, it is possible to prevent moisture or soot once attached to the inside protector 120 (inside tube-shaped portion 160) from again being included in gas introduced to the detecting element 10 from the inside gas introducing portion 170, and it is possible to suppress moisture or soot from becoming attached to the detecting element 10.

The invention is not limited to the above embodiments, and various modifications may be practiced within the spirit and scope of the claims appended hereto. For example, a variety of modified examples will be described by reference to FIGS. 8 and 9.

Figures 8A, 8B:
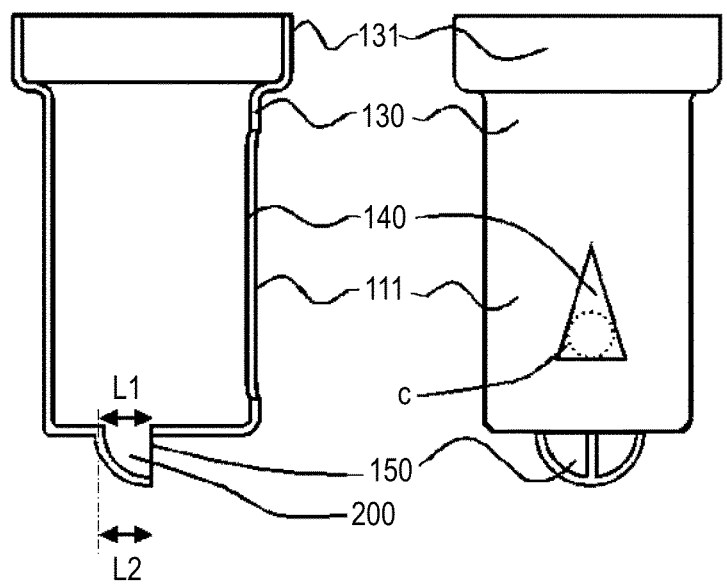
FIG. 8A and FIG. 8B show the outside protector 111 in a modified example.

FIG. 8A is a view of the outside protector 111 in a modified example when seen from the downstream side of the intake passage 2, and FIG. 8B is a vertical cross-sectional view of the outside protector 111 in the modified example. As shown in FIG. 8, the first opening 140 may have a triangular shape instead of a slit shape, and may have an oval shape, a polygonal shape, a T-slit shape, or the like while not shown. Meanwhile, the number of first openings 140 provided is preferably one, but may be plural. The first opening 140 may be formed in any manner as long as the shape and dimensions of the opening in the second opening 150 are determined based on the imaginary circle C (diameter R), which is the largest circle that can come into contact with the inside of the first opening 140.

In addition, as shown in FIG. 8, the number of the second opening 150 formed may be plural. In the present modified example, two second openings 150 are formed. In addition, while the second opening 150 in FIG. 8 is not formed so that the imaginary circle C can be drawn therein, the total of the opening area is formed so as to exceed the area ($\pi^2/4$) of the imaginary circle C, and therefore it is possible to suppress soot from clogging the second opening 150. Meanwhile, the aspect ratios of the two second openings 150 shown in FIG. 8 are about 1.4 respectively. In addition, in the embodiment, since the second opening 150 is formed so that L0=1 (L1=L2), it is not possible to visibly observe the second opening 150 and the inner space of the protector 100 even when the outside protector 111 is seen from the leading end side along the central axis. Meanwhile, the second opening 150 in the embodiment is formed to have only the central portion of the outside bottom portion 132 protruding toward the leading end side in the axial direction.

Figure 9A:
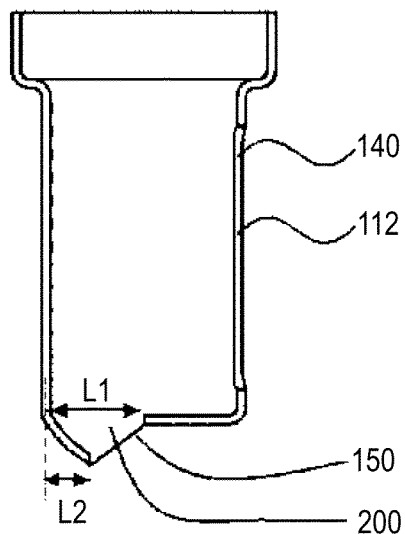
FIG. 9A and FIG. 9B show cross-sectional views of the outside protectors 112 and 113 in the modified example.
Figure 9B:
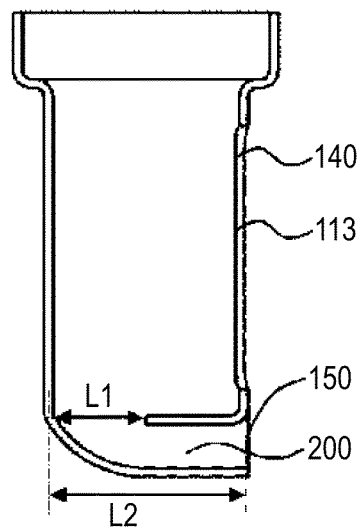

In addition, the outside bottom portion 132 may be formed as shown in FIG. 9. In FIGS. 9A and 9B, the second opening 150 is formed so as to face the downstream side of the intake passage 2 by adjusting L0=0.5 and L0=2.0 respectively.

Figure 10:
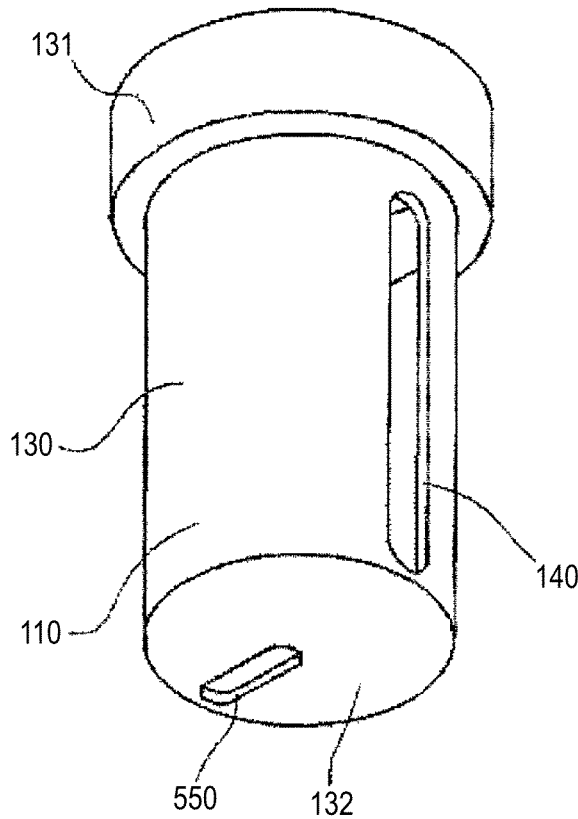
FIG. 10 shows a perspective view of the outside protector 500 in a related art example.

In FIG. 9A, when the gas sensor 1 is seen from the leading end side along the axial direction, the inner space of the protector 100 (outside protector 112) can be visibly observed through the second opening 150, but the visually observable inner space is small in comparison to a protector of the related art in which the second opening 550 faces the leading end side in the axial direction as shown in FIG. 10. Specifically, the dimensions of the opening seen from the diameter direction of the protector 100 are reduced to half. Therefore, it is possible to suppress moisture and the like from intruding into the inside of the gas sensor in comparison to the second opening 550 facing the leading end side in the axis direction as shown in FIG. 10.

Meanwhile, the "radial direction of the protector 100" refers to a direction on a straight line passing the planar face intersecting the central axis of the protector 100 and passing the central axis of the protector 100.

In FIG. 9B, it is not possible to visibly observe the second opening 150 and the inner space of the protector 100 (outside protector 113) even when the gas sensor 1 is seen from the leading end side along the axial direction. Therefore, it is possible to more effectively suppress moisture and the like from intruding into the inside of the gas sensor 1.

Meanwhile, the second bottom wall portion 1322 may be formed in a deformed manner so that a part of the bottom portion 132 protrudes in the axis direction, and may be formed by fixing to the first bottom portion 1321 by welding or the like.

Experiment Results:

FIG. 11 is a view explaining an evaluation experiment in which the influence of the distance A and the distance B on the amount of water covering the leading end portion is investigated. FIG. 11A is a view showing the first experiment results of the evaluation experiment, and FIG. 11B is a view for explaining the testing method of the evaluation experiment 1. In addition, FIG. 11C is a view showing the form of the leading end portion of a ceramic laminated body after the evaluation experiment, FIG. 11C-1 is a partial enlarged photograph of the leading end portion of the ceramic laminate, and FIG. 11C-2 is the image-treated partial enlarged photograph of the leading end portion of the ceramic laminate.

In the evaluation experiment 1, five gas sensors 1 having different L2/L1 values were prepared, respectively, and evaluated by carrying out water-covering tests. However, the tests were carried out with sheet-form (planar sheet-shaped) ceramic laminates (corresponding to the detecting element 10 of the embodiment) assembled instead of the bottomed tube-shaped detecting element 10 of the gas sensor 1. This was to facilitate computation of the amount of covering water as described below. As shown in FIG. 11B, the water-covering test was carried out by mounting the gas sensor 1 in a pipe 80 having an inner diameter of 50 mm, and spraying a predetermined amount of water Wa to the ceramic laminated body from spray nozzles 82 provided in the pipe 80. In addition, the surface of the ceramic laminated body is coated with carbon in advance for evaluation in the water-covering test. Meanwhile, the portion of the ceramic laminated body coated with carbon is a portion on the leading end side of the portion held by the ceramic ring 21 (FIG. 1), and a portion exposed to the inside of the pipe 80 (hereinafter, the exposed portion is also referred to as a "detecting portion"). Specifically, the detecting portion has a size of 4 mm in width and 15 mm in length. The water-covering test was carried out under conditions that the distance L from the nozzle 84 to the axis 0 of the gas sensor 1 was 150 mm, gas flowing in the pipe 80 was air, the flowing rate of the air was 30 m/s, and the flowing direction of the air was the direction facing the gas sensor 1 from the spray nozzle 82. In addition, the water-covering test was carried out by repeating a spraying process in which 30 ml of water Wa was sprayed for 5 seconds at a spraying pressure of 0.2 MPa three times at predetermined intervals.

After the water-covering test, the gas sensor 1 was taken out from the pipe 80, and the place on the detecting portion of the ceramic laminated body hit by the water Wa in carrying out the spraying process three times was identified by treating images of the detecting portion. Specifically, in contrast to the photograph of the detecting portion before the image treatment as shown in FIG. 11C-1, in the detecting portion, the portion AW where the water Wa hit was image-treated to white, and the portion where the water Wa did not hit was image-treated to black as shown in FIG. 11C-2, whereby the portion AW where the ceramic laminated body hit by water Wa was identified. Next, in the surface of the detecting portion, the fraction of the place AW where the water Wa hit was obtained from formula (1) below, and the value thus obtained was taken as the amount of covering water Wb (%).

$$Wb = (Aw/B) \times 100 \quad (1)$$

Here, 'Wb' is the amount of covering water (%), 'Aw' is the area (mm$^2$) where the water Wa hit the ceramic laminated body (white), and 'B' is the surface area (mm$^2$) of the detecting portion.

In the evaluation test 1, those gas sensors 1 showing favorable results of 2.0% or less in the amount of covering water Wb were counted as OK products, and the gas sensors 1 showing unfavorable results of more than 2.0% in the amount of covering water Wb were counted as NG products. Here, the reason why the threshold value of the amount of covering water Wb was set to 2.0% is that little cracking occurred in the gas sensor 1 having an amount of covering water Wb of 2.0% or less when the gas sensor 1 was used in the exhaust gas pipe.

As shown in FIG. 11A, when L2/L1 is 0.25, the number of OK products is not changed from that of the related art products, and, when L2/L1 is 0.5 or more, the number of the OK products is increased as compared with that of the related art products. Therefore, when the relationship L2/L1≥0.5 is satisfied, intrusion of moisture and the like into the inside of the gas sensor can be suppressed, and it is possible to effectively suppress cracking or fracturing of the detecting element.

The water-covering tests were carried out under stricter conditions in the evaluation experiment 2 than in the evaluation experiment 1. FIG. 11E is a view explaining the testing method of the evaluation experiment 2. The only difference from the evaluation experiment 1 is that the bottom portion of the gas sensor 1 was mounted in the pipe 80 at a slope of 30° in the direction of the spray nozzle 82, and the other conditions were the same and thus will not be described.

As shown in FIG. 11D, the present experiment conditions are severe conditions under which even the sample having an L2/L1 of 0.5, which is an OK product in the evaluation experiment 1, is evaluated as an NG product. However, even under the experiment conditions, when L2/L1 is 1.0 or more, the number of OK products is increased. Therefore, it is possible to further suppress intrusion of moisture and the like into the inside of the gas sensor and more effectively suppress cracking or fracturing of the detecting element by satisfying the relationship L2/L1≥1.0.

In addition, the embodiment and the modified example employed a universal exhaust gas oxygen sensor as examples, but the invention can be similarly applied to a protector mounted in an oxygen sensor, an NO$_X$ sensor, an HC sensor, a temperature sensor, and the like.

In addition, in the embodiment and the modified example, the axial direction in which the detecting element 10 extends was the same as the central axis of the protector 100. However, the invention is not limited thereto. Furthermore, in the embodiment, the mounting angle of the gas sensor 1 in the intake passage 2 forms a right angle. However, the invention is not limited thereto, and the leading end side (bottom portion side) of the protector may face the leading end side in the vertical direction, and the first opening 140 and the second opening 150 may be disposed so as to face the downstream side of the intake passage 2.

In addition, in the embodiment and the modified example, the first bottom wall portion 1321 and the leading end of the outside tube portion 130 are present at the same location when viewed in the axial direction. However, the invention is not limited thereto. In summary, the entire first bottom wall portion 1321 may protrude to a greater extent than the outside tube portion 130 toward the leading end side as long as at least a part of the inner face of the second bottom wall portion 1322 protrudes further than the outer face of the protruding first bottom wall portion 1321 toward the leading end side.

This application claims priority from Japanese Patent Application No. 2010-253403, which was filed on Nov. 12, 2010, and from Japanese Patent Application No. 2011-223562, which was filed on Oct. 11, 2011, the disclosures of which are incorporated herein by reference in their entirety.

What is claimed is:

1. A gas sensor adapted for disposing in an intake passage of an internal combustion engine, which comprises:
    a detecting element extending in an axial direction and comprising a detecting portion for detecting a specific gas component in a gas to be measured on a leading end side of the gas sensor; and
    a protector having a tube portion surrounding the detecting portion from outside in a radial direction and a bottom portion connected to a leading end side of the tube portion, the protector having a first opening which is disposed at the tube portion so as to only face the downstream side of the intake passage in the internal combustion engine, and which allows the gas to be measured to flow into the tube portion, and a second opening at the bottom portion through which the gas to be measured flows, and
    wherein the second opening is formed as a protruding part outside the bottom portion,
    wherein the bottom portion includes a first bottom wall portion and a second bottom wall portion,
    the second bottom wall portion protrudes toward the leading end side in the axial direction, and at least a part of an inner face of the second bottom wall portion is located at the leading end side in the axial direction with respect to an outer face of the first bottom wall portion,
    the second opening, which is visible when viewed from the downstream side of the intake passage, is provided on a side opposite the inner space of the tube portion in a communication passage formed by the inner face of the second bottom wall portion, and
    the communication passage is formed so that an opening area of the second opening is larger than an area of a largest imaginary circle that can be placed inside the first opening when the first opening is viewed planarly in a direction perpendicular to the central axis of the tube portion, and
    wherein all the openings in the protector only face the downstream side of the intake passage in the internal combustion engine.

2. The gas sensor as claimed in claim 1, wherein a minimum value L1 of the distance between a first end portion farthest separated from an end edge of the second opening in the second bottom wall portion and the first bottom wall portion in the diameter direction of the protector and,
    a minimum value L2 of the distance between the first end portion and an end edge of the second opening in the second bottom wall portion in the diameter direction of the protector satisfy a relationship of L2/L1≥0.5.

3. The gas sensor as claimed in claim 2, wherein the minimum value L1 and the minimum value L2 satisfy a relationship of $L2/L1 \geq 1.0$.

4. The gas sensor as claimed in claim 1, wherein the second opening has a size large enough to include the entire imaginary circle.

5. The gas sensor as claimed in claim 1, wherein the second opening has an aspect ratio of 5 or less.

6. The gas sensor as claimed in claim 1, wherein the bottom of the protector has a single second opening.

7. The gas sensor as claimed in claim 1, adapted to operate such that the temperature in at least a portion of the protector is 280° C. to 600° C.

8. The gas sensor as claimed in claim 1, wherein the first opening and the second opening are the only openings in the protector.

* * * * *